(12) United States Patent
Glaser

(10) Patent No.: US 7,731,728 B2
(45) Date of Patent: Jun. 8, 2010

(54) INTERNAL LIMITING MEMBRANE RAKE

(76) Inventor: Bert M. Glaser, 901 Dulaney Valley Rd., Suite 200, Towson, MD (US) 21204

( * ) Notice: Subject to any disclaimer, the term of this patent is extended or adjusted under 35 U.S.C. 154(b) by 542 days.

(21) Appl. No.: 11/105,342

(22) Filed: Apr. 14, 2005

(65) Prior Publication Data

US 2006/0116703 A1 Jun. 1, 2006

Related U.S. Application Data

(60) Provisional application No. 60/631,509, filed on Nov. 30, 2004.

(51) Int. Cl.
*A61B 17/24* (2006.01)
*A61F 9/00* (2006.01)
*A61F 11/00* (2006.01)

(52) U.S. Cl. .................................... 606/161

(58) Field of Classification Search ............... 606/107, 606/131, 156, 159, 161, 162; D24/150, 107
See application file for complete search history.

(56) References Cited

U.S. PATENT DOCUMENTS

| | | | | |
|---|---|---|---|---|
| 4,174,715 | A * | 11/1979 | Hasson | 606/206 |
| 4,483,133 | A * | 11/1984 | Pasley | 56/400.06 |
| 5,053,041 | A * | 10/1991 | Ansari et al. | 606/148 |
| 5,868,728 | A | 2/1999 | Giungo et al. | |
| 6,017,353 | A * | 1/2000 | Rankins | 606/162 |
| 6,361,540 | B1 * | 3/2002 | Gauderer et al. | 606/106 |
| 6,453,906 | B1 * | 9/2002 | Taylor et al. | 128/898 |
| 6,488,695 | B1 * | 12/2002 | Hickingbotham | 606/206 |
| 6,575,989 | B1 * | 6/2003 | Scheller et al. | 606/161 |
| 6,730,076 | B2 * | 5/2004 | Hickingbotham | 606/16 |
| 6,886,565 | B2 * | 5/2005 | Morris et al. | 128/846 |
| 2002/0095161 | A1 * | 7/2002 | Dhindsa | 606/120 |
| 2003/0040773 | A1 | 2/2003 | Arumi et al. | |
| 2003/0120305 | A1 | 6/2003 | Jud et al. | |

FOREIGN PATENT DOCUMENTS

EP 0864310 A2 9/1998

* cited by examiner

*Primary Examiner*—(Jackie) Tan-Uyen T. Ho
*Assistant Examiner*—Dianne Dornbusch
(74) *Attorney, Agent, or Firm*—Arent Fox LLP

(57) ABSTRACT

A medical device for removing a thin membrane from the inner surface of an eye. The device comprises a rake that includes a handle having a hollow body from which a slide member telescopes. A plurality of tines are provided on a free end of the slide member, wherein each tine includes a tissue engaging feature provided on a free end of each tine. The tines are extended and retracted from an end of the handle, such that, when completely retracted, only the tissue engaging features protrude from the handle or all tissue engaging features can be retracted into the handle. In operation, the rake is manipulated along an upper surface of the membrane until the tissue engaging features engage the membrane. Once the tines engage the membrane, the rake is moved upward and tangentially away relative to an upper surface of the retina until the membrane is removed therefrom.

18 Claims, 8 Drawing Sheets

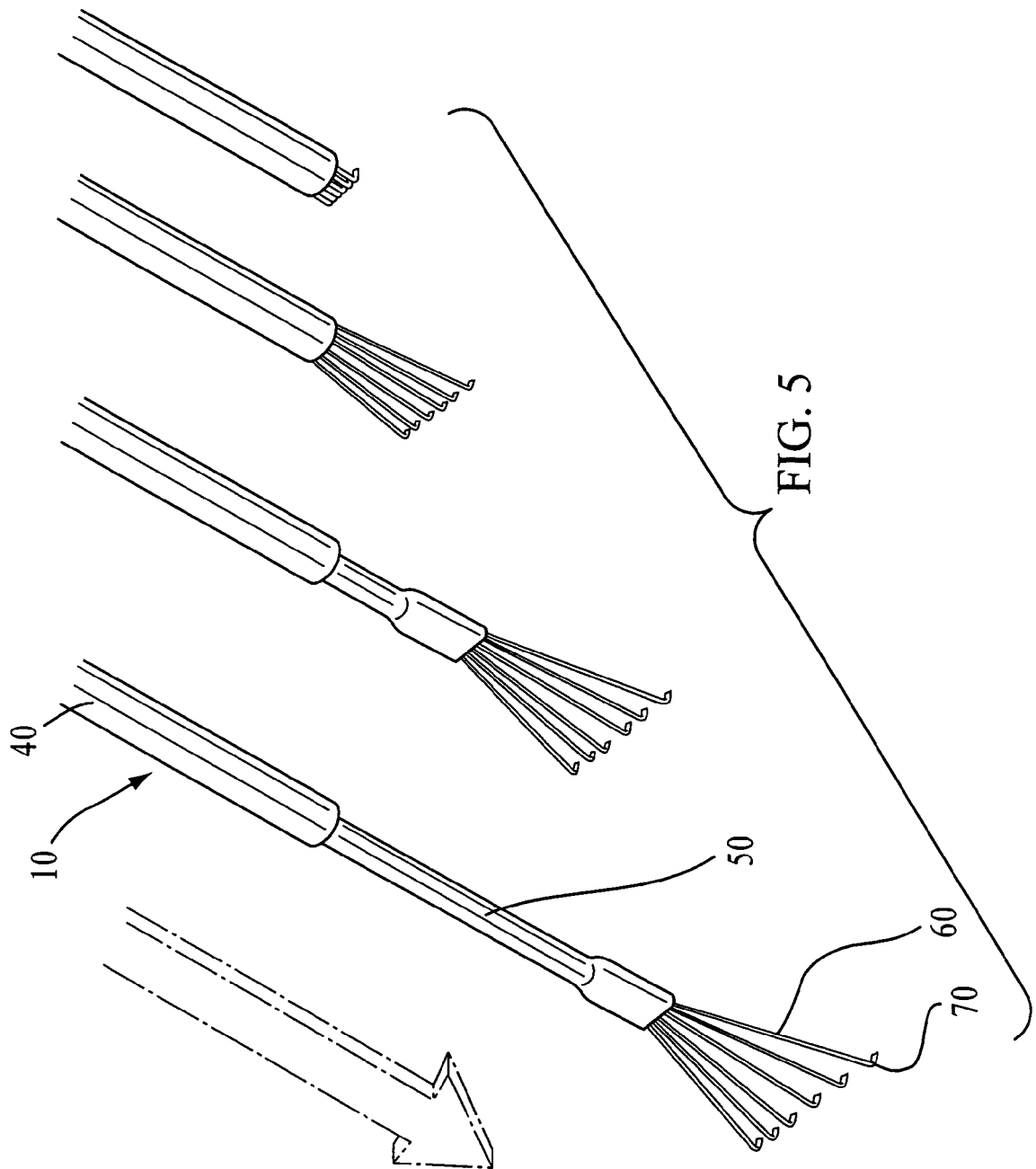

INTERNAL LIMITING MEMBRANE RAKE

CROSS-REFERENCE TO RELATED APPLICATIONS

This application claims the benefit of Applicant's U.S. Design Application No. 29/215,250, entitled "Internal Limiting Membrane Rake", filed Oct. 15, 2004, now abandoned; and U.S. Provisional Application No. 60/631,509, entitled "Internal Limiting Membrane Rake," filed Nov. 30, 2004, which are hereby incorporated by reference in their entirety.

BACKGROUND OF THE INVENTION

1. Field of the Invention

The present invention relates to a medical device used for removing a membrane provided on an inner surface of a retina of an eye.

2. Discussion of the Related Art

Certain diseases involve the presence of a thin membrane of scar tissue that must be removed via a medical procedure. Examples of these procedures are the peeling of epiretinal membranes and possibly internal limiting membranes that are the result of idiopathic epiretinal membranes. These membranes may also be associated with macular holes and in vitreo macular traction syndrome, the peeling of epiretinal membranes in diabetic retinopathy, peeling of epiretinal membranes in proliferative vitreo retinopathy, peeling of epiretinal membranes after trauma, and the peeling of epiretinal membranes after intraocular inflammation, including uveitis and ophthalmitis.

Currently, these procedures are typically performed using one of three types of medical devices. Referring to FIG. 1(a), the first type is a sharp pick 1 comprising a needle 2, typically of size 20 to 23 gage, that is bent at one end. The bent end of the needle 2 forms a sharp point 3, which is used to engage the membrane 20. However, prior to using the sharp pick 1, a small incision often must be made in the membrane 20, as shown by the arrow in FIG. 1(a). Thereafter, the sharp pick 1 is inserted into the incision where the pick 1 is used to scrape along an edge of the incision between an inner surface of the retina 30 and a lower surface of the membrane 20 in an attempt to lift up the membrane 20 in a direction indicated by the arrows of FIG. 1(b).

However, the pick 1 has drawbacks. In particular, the pick 1 is able to engage a relatively small area of the membrane 20, making removal of all or large portions of the membrane 20 at the same time extremely problematic.

Referring to FIG. 2, the second medical device currently used to remove the membrane 20 is a pair of forceps 4, which are used to clamp a small portion of the membrane 20 along an outer edge or along an edge of an incision made therein. The forceps 4 grip the portion of the membrane 20 and lift the membrane 20 off of the retina 30. Because the forceps 4 engage such a small portion of the membrane 20, the forceps 4 have difficulty removing the membrane 20 in one piece and imparts the risk of leaving behind pieces of the membrane.

Referring to FIG. 3, the third medical device currently used to remove retinal membranes is a scraper 5, which commonly includes a piece of silicon tubing 6 with small pieces of diamonds 7 embedded onto an outer surface of the tubing 6. A region of the tubing 6 having the diamond pieces 7 embedded therein is applied to and scraped along an inner surface of the membrane 20, as indicated by the arrow in FIG. 3. The scraping action dislodges the membrane 20 from the surface of the retina 30. However, the scraping action requires downward pressure to be exerted on the retina 30, which creates a substantial risk of injury to the retina 30 and adjacent structures. Similarly, the scraper 6 is only able to engage a small area of the membrane 20, making removal of the membrane 20 in one piece very difficult and increasing the possibility of leaving pieces of the membrane behind. Finally, the scraper 6 necessitates the insertion of an additional instrument (not shown) into the eye to complete removal of the membrane 20 from the retina 30.

An additional drawback associated with each of the above devices, that is, the pick 1, the forceps 4, and the scraper 6, is that relatively high magnification levels must be used during the corresponding procedures for removing the membrane 20. The high magnification levels inherently decrease the area of the retina 30 that can be viewed by medical personnel when attempting to remove the membrane 20, thereby extending the time necessary to perform the procedure as well as making it more difficult for the medical personnel to successfully remove the membrane 20 in a single piece.

SUMMARY OF THE INVENTION

The present invention addresses the above-discussed and other drawbacks in the known medical devices. The present invention provides a membrane rake which engages any region of the membrane along a large surface area of the membrane and is not limited to engaging an edge of the membrane or the edge of an incision made in the membrane. Moreover, the structural configuration of the membrane rake permits the user to engage a much larger surface area of the membrane than any of the known medical devices.

Furthermore, the present invention does not require the formation of an incision in the membrane or the introduction of an additional instrument into the eye to aid or complete the process of removing the membrane from the retina of the eye. Moreover, the present invention applies significantly less pressure onto the retina when initially engaging the membrane relative to the pressure applied onto the retina by some of the known medical devices described above. Additionally, once the present invention has engaged the membrane on the retina, relatively minimal tangential and lifting forces are applied to the retina when using the present invention to remove the membrane from the retina.

Finally, the present invention is used at lower magnification levels relative to the relatively higher magnification levels which the known medical devices must be used, thereby providing a significantly larger field of view during the membrane removal procedure. The aforementioned benefits and features of the present invention greatly reduce the risk of injury to the eye while significantly simplifying the process of removing the membrane from the retina, as well as increasing the likelihood the membrane is removed entirely in a single piece.

To achieve the aforementioned and other benefits, the present invention provides a rake configured to remove a thin membrane formed on an inner surface of a retina of an eye. In one embodiment, the rake includes a handle and a plurality of tines which are retractable into and extendable from the handle either manually or mechanically. Ideally, the handle has a hollow body and at least one barb or other such tissue engaging mechanism is provided on a tip of each tine.

According to one embodiment of the invention, the tines are slidingly retracted into the hollow handle body as well as slidingly extended from the hollow handle body. Once extended from a working end of the handle body, the tines spread apart and outward from each other. As such, the rake is able to engage a relatively large area of the membrane surface.

In another embodiment of the present invention, the tines are flexible, wherein the flexibility of the tines depend on the amount the tines are extending from the working end of the handle body. The farther the tines extend from the working end of the handle body, the greater the amount of flexibility. Similarly, the closer the tines are to the working end of the handle body, that is, the less the tines are extended from the working end of the handle body, the lesser the amount of flexibility the tines posses.

According to another aspect of the present invention, once the extended tines engage the upper surface of the membrane, the tines are retracted, drawing up and securing the membrane between the at least one barb or other tissue engaging feature and the working end of the handle.

Additional advantages and novel features of the present invention will be set forth in the following description, and will also become apparent to those skilled in the art upon examination of the following or upon learning by practice of the invention.

BRIEF DESCRIPTION OF DRAWINGS

Other aspects of the present invention will be better understood from the following description, along with the accompanying drawings, wherein:

FIG. 5 is a diagram illustrating the different states in which the tines of the rake shown in FIG. 4 can be extended from the handle of the rake

DETAILED DESCRIPTION OF THE INVENTION

The present invention provides a membrane rake 10 which engages any region of the membrane 20 along the entire surface of the membrane 20. The structural configuration of the membrane rake 10 permits the user to engage a much larger surface area of the membrane 20 than any of the known medical devices. Furthermore, the present invention does not require the formation of an incision in the membrane 20 or the introduction of an additional instrument into the eye to aid or complete the process of removing the membrane 20 from the retina 30 of the eye. Moreover, the rake 10 applies significantly less pressure onto the retina and adjacent structures when initially engaging the membrane 20 relative to the pressure applied onto the retina by some of the known medical devices described above. Finally, the rake 10 is used at lower magnification levels relative to the relatively higher magnification levels which the known medical devices must be used, thereby providing a significantly larger field of view during the membrane removal procedure.

Figure 1A:
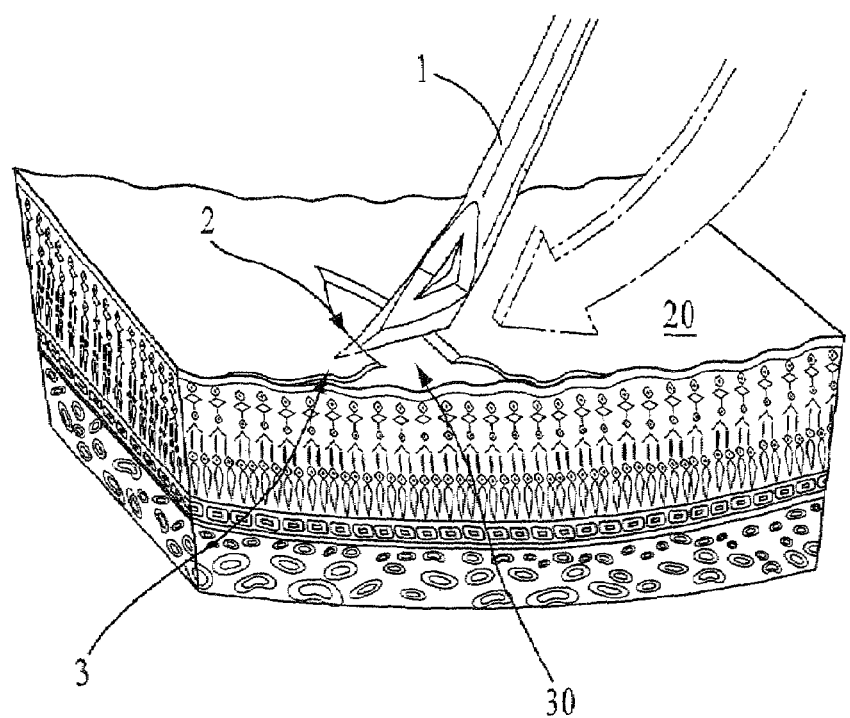
FIGS. 1(a) and 1(b) illustrate a conventional sharp pick device used to remove a membrane from a retina.
Figure 1B:
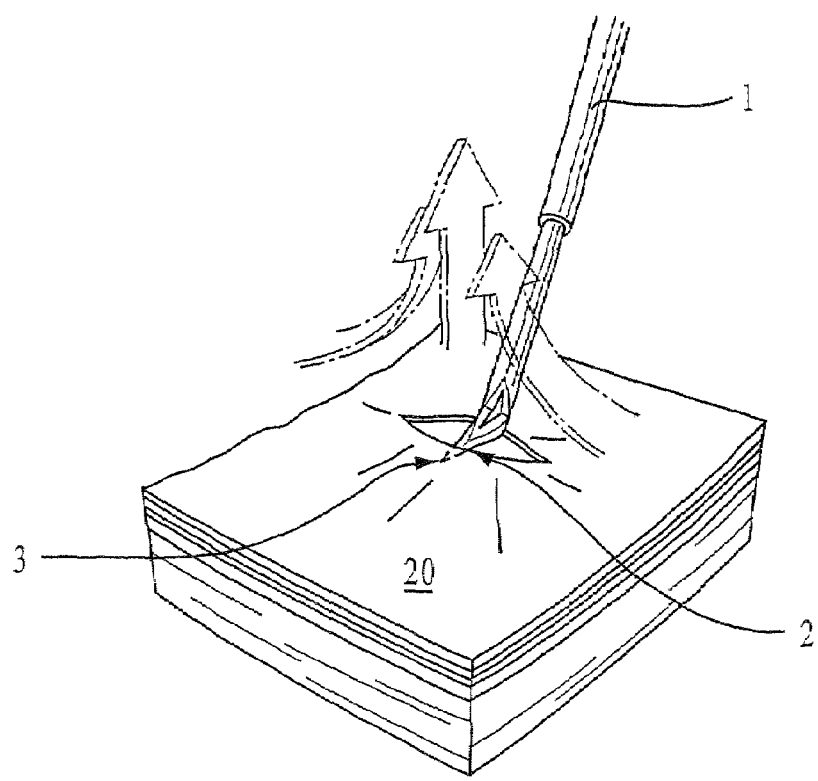
Figure 2:
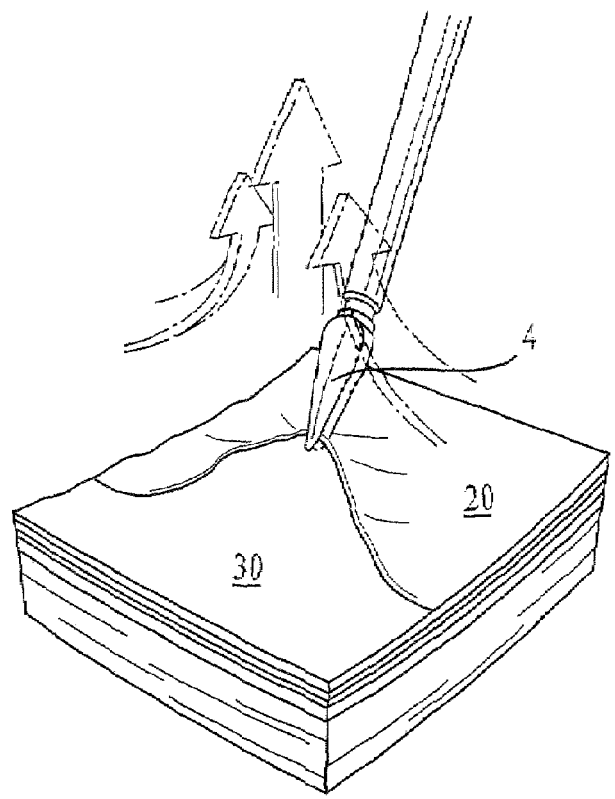
FIG. 2 illustrates a conventional forceps device used to remove the membrane from the retina.
Figure 3:
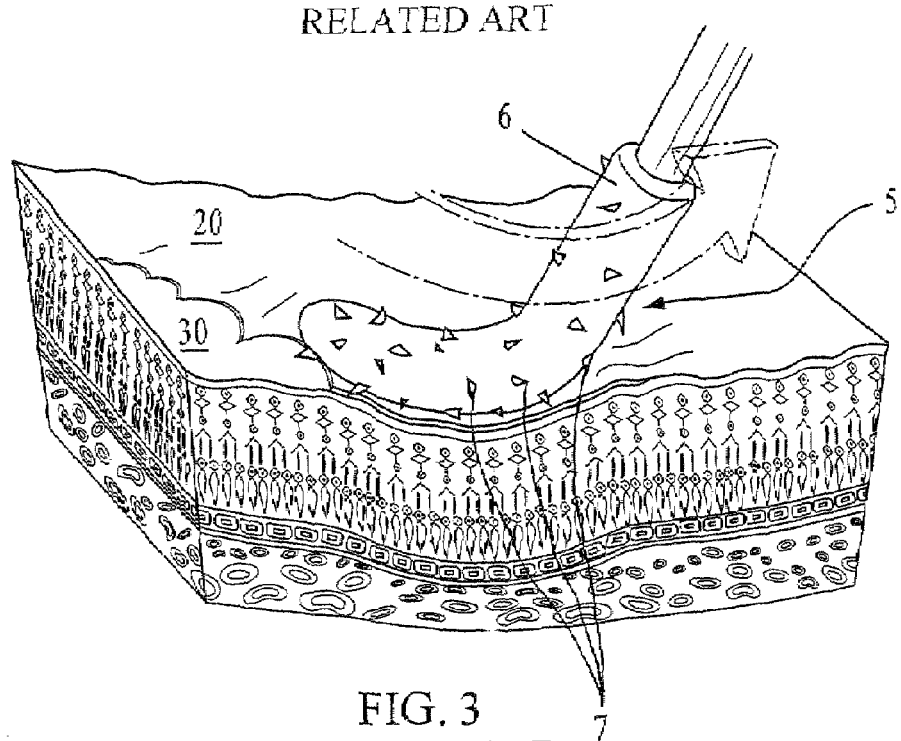
FIG. 3 illustrates a conventional scraper device used to remove the membrane from the retina.
Figure 4:
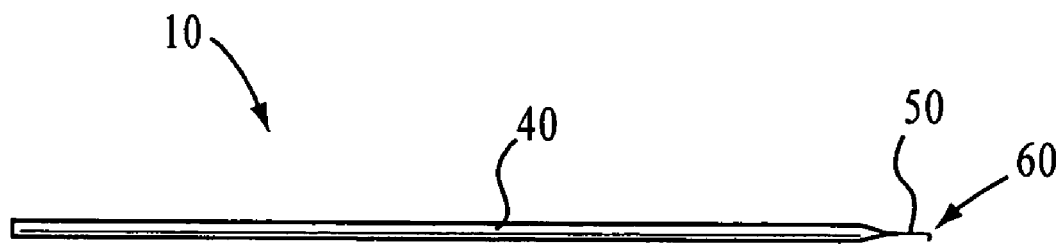
FIG. 4 is a cross-sectional view of a rake according to an embodiment of the present invention.

FIG. 4 illustrates an exemplary rake 10 of an embodiment of the present invention, for use in removing a membrane 20 (FIGS. 6 and 8-10) from an inner surface of the retina 30 (FIGS. 6 and 8-10) of the eye. The rake 10 of this embodiment comprises a handle 40 and a telescoping slide member 50. The handle 40 comprises a hollow tube, through which the slide member 50 telescopes freely within an interior surface of the handle 40 (e.g., a central opening extending the length of the handle). Although the body of the handle 40 is preferably tubular, it should be noted that it is within the scope of the invention to provide the body of the handle 40 with any suitable geometric shape that promotes gripability of the handle 40, such as, for example, oval, rectangular, trapezoidal, hemi-spherical and the like in cross-section.

Fixedly provided at an end of the slide 50 are multiple tines 60 each having one end attached to the slide 50, with the opposite end freely extending therefrom. A free end of each tine 60 has a barb or other tissue engaging feature 70 (FIGS. 5-6) provided thereon.

As shown in FIG. 5, the rightmost rake 10, when the slide member 50 is fully retracted, such that the slide member 50 and most of the length of the tines 60 are contained within the body of the handle 40, the tissue engaging features 70 protrude from the end of the handle 40. As shown in the second from the right rake 10 in FIG. 5, as the tines 60 extend from the handle 40, the outer ends of the tines 60 spread apart from each other and away from a longitudinal axis of the rake 10, allowing the tissue engaging features 70 to separate from one another in an unobstructed manner. Once fully extended, as shown in the third from the right rake 10 in FIG. 5, tines 60 increase the potential area of engagement, providing for better control when removing the membrane 20. Finally, the leftmost rake 10 shown in FIG. 5 illustrates the feature of the fully extended tines 60, wherein the slide member 50 telescopes or slides out of the body of the handle 40.

In this embodiment, the amount the tines 60 are permitted to extend beyond the handle 40 is effectuated by pulling/pushing on an end of the slide member 50 that is opposite the end from which the tines 60 extend. It will be recognized by those familiar with the art that, for embodiments of the present invention incorporating extending and spreading tines, alternate features to provide such extension and spreading may be used. For example, the tines may be retracted or extended from the handle without the use of a slide member. Further, while the relative position of the slide member 50 and handle 40 of FIG. 5 are maintained by simple frictional engagement between the slide member 50 and the handle 40, other features may be provided to maintain the relative position, such as locking pins within openings, screw retainers, clips engaging slots, and the like, including mechanical, hydraulic, and electromechanical mechanisms.

Figure 6A:
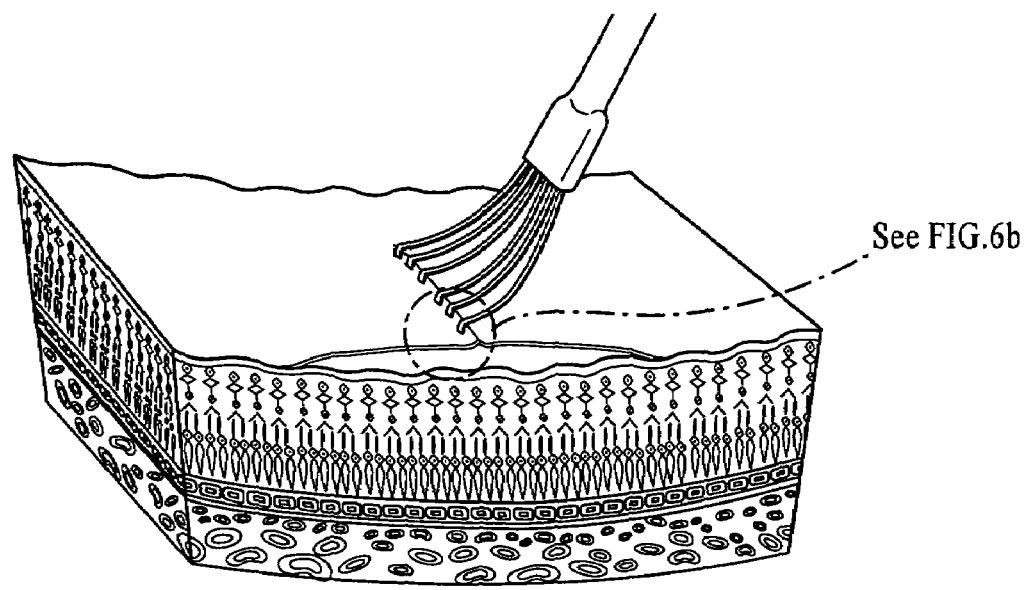
FIG. 6 illustrates an embodiment of the tissue engaging features provided at the free end of each tine.
Figure 6B:
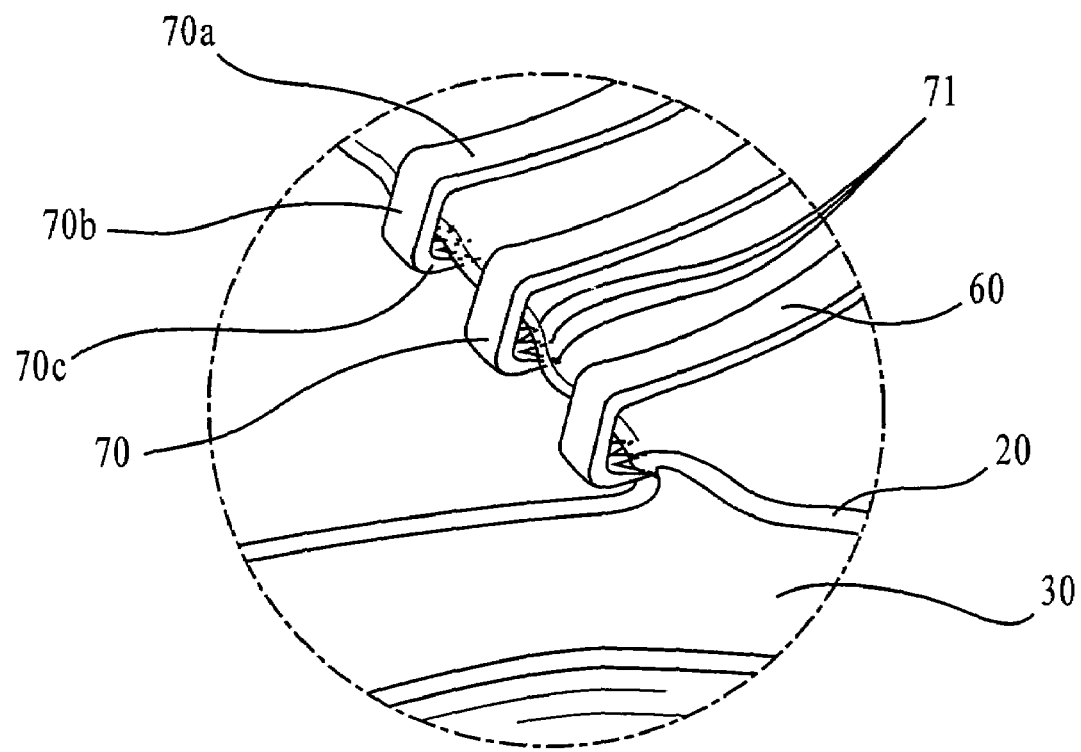

Referring to FIG. 6, in one embodiment of the present invention, the tissue engaging features 70 comprise a plurality of serrated barbs 71 extending from the free end of each tine 60. As shown in FIG. 6, each tissue engaging feature 70 includes a flexible body portion 70a joined to an engaging portion 70c by a transverse portion 70b. In a fully retracted state, the transverse portion 70b extends orthogonally relative to the longitudinal axis of the rake 10. Further, while in the fully retracted state, the engaging portion 70c extends in a direction that is parallel relative to the longitudinal axis of the rake 10 and opposite to the direction in which the slide member 50 telescopes away from the body of the handle 40. Also, as shown in FIG. 6, at least one and preferably a plurality of barbs 71 are provided on a free end of each engaging portion 70c of the tine 60. Additionally, in the embodiment of the FIG. 6, the tissue engaging features 70 may include a serrated end to increase friction or other gripping engagement with a surface of the membrane 20.

Figure 7:
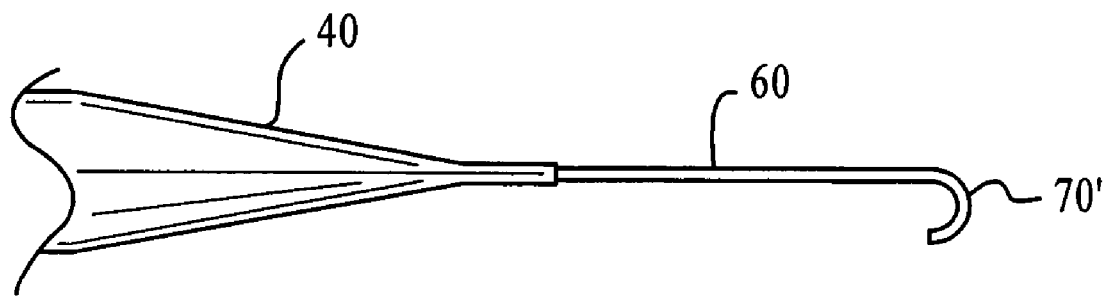
FIG. 7 illustrates another embodiment of the tissue engaging features provided at the free end of each tine.

Although FIG. 6 illustrates the barbs 71 as having pointed or serrated bodies, it should be noted that it is within the scope of the invention for the barbs 71 to have any suitable geometric shape that will promote the gripping and lifting of the membrane 20 off of the retina 30. For example, in an envisioned alternate variation (not shown), the tissue engaging features 70 of the embodiment of FIG. 6 are not serrated but, rather, have a sharpened unserrated edge. In yet another example, FIG. 7 illustrates another embodiment of the present invention wherein the tissue engaging features 70' are curved.

Figure 8:
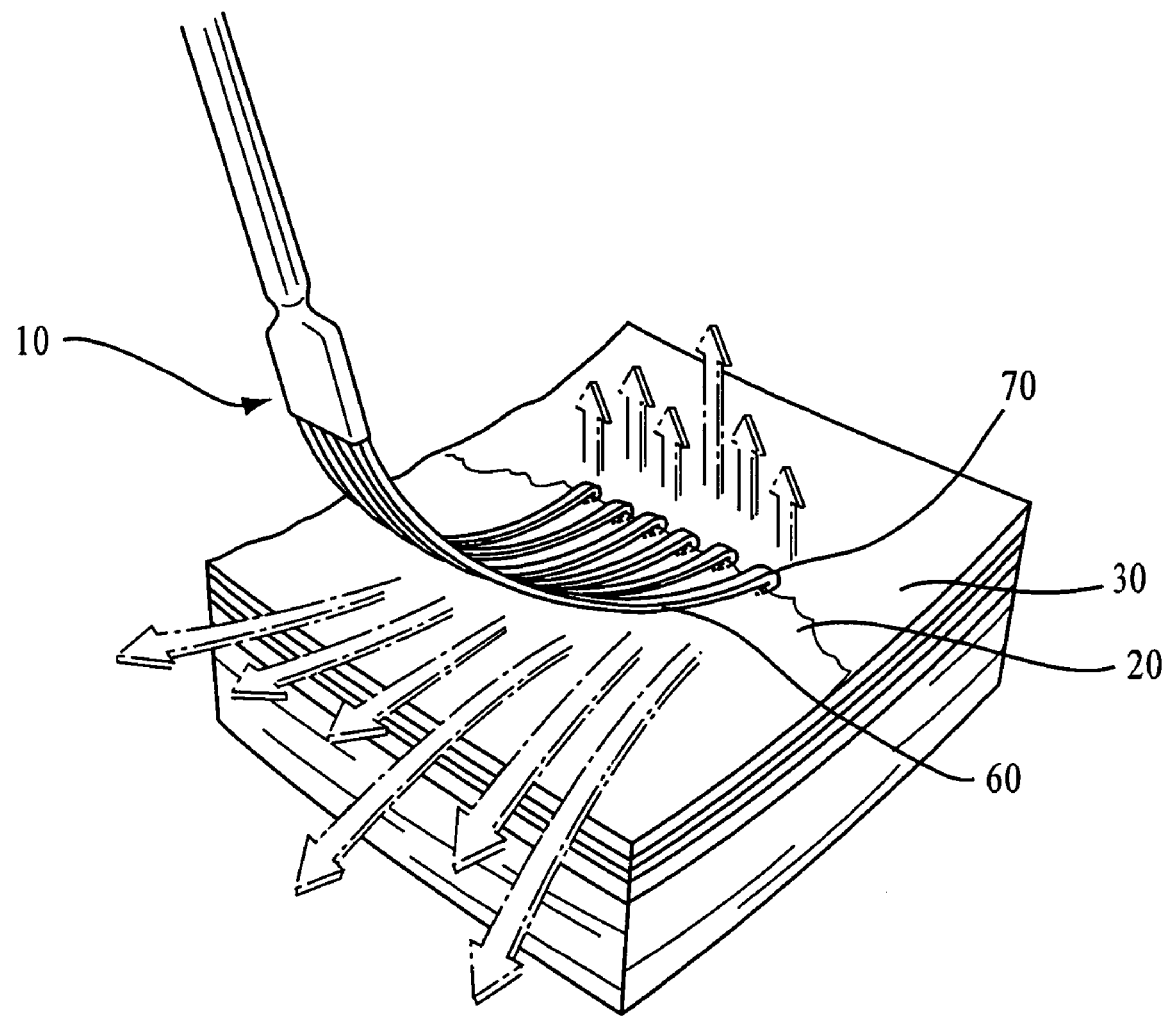
FIG. 8 illustrates the tangential and lifting forces created by the rake of the present invention that are used to remove a membrane from the retina of an eye.

As shown in FIG. 8, when engaged with the membrane 20, the tissue engaging features 70 and 70' create tangential and lifting forces to remove the membrane 20 and reduce downward pressure on the retina 30 as illustrated by the arrows. The extension and retraction of the tines 60 into and out of the handle 40, in combination with the tissue engaging features 70 and 70', offers yet another benefit. In particular, once the extended tines 60 engage the membrane 20, the tines 60 can thereafter be retracted, drawing up and clamping the membrane 20 between the tissue engaging features 70 and 70' and the end of the handle 40 from which the slide member 50 telescopes. Such clamping action further reduces the need to introduce a second instrument into the eye for removing the membrane 20. Further, the ability to retract the tines 60 into the handle 40 decreases the likelihood that the inner surface of the retina 30 and any other part of the eye may be damaged by the tines 60, by retracting the tines 60 when the rake 10 is inserted or withdrawn from the eye.

Figure 9:
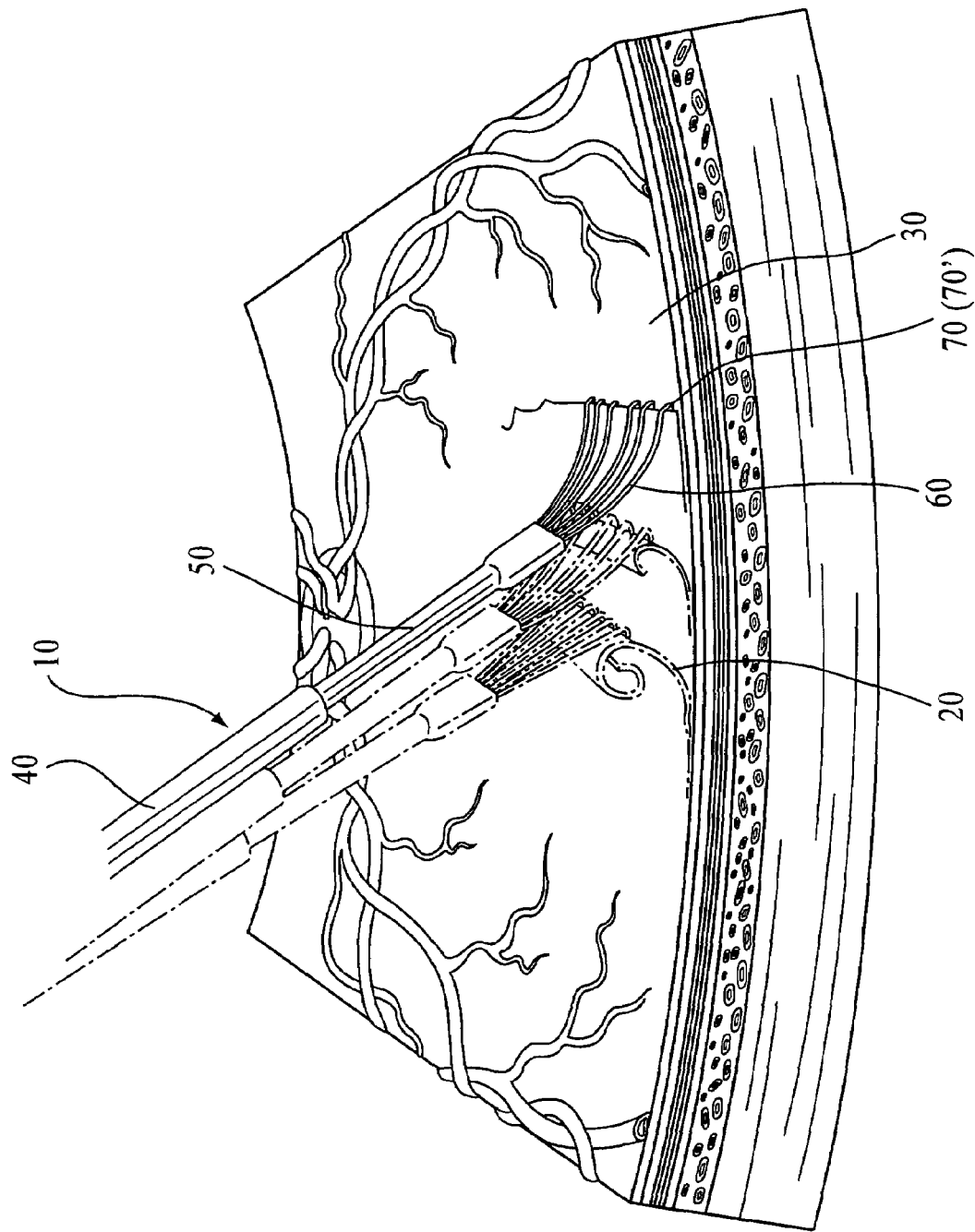
FIG. 9 illustrates the different states of the rake engaging the membrane on the retina of an eye and removing the membrane therefrom.

FIG. 9 illustrates an exemplary rake 10 removing a membrane 20 from the surface of the retina 30. The right-most representation of the rake 10 of FIG. 9 shows the tissue engaging features 70 and 70' engaging an edge of the membrane 20. The progression of figures of the rake 10, from right to left, as shown in FIG. 9, depicts how the rake 10 may be used to both pull and lift the membrane 10. FIG. 9 also shows the tines 60 flexing, in accordance with some embodiments of the present invention.

In the embodiment of FIG. 9, the further the tines 60 are extended from the handle 40, the more the tines 60 are able to flex when pressed against an object. The increased flexibility of the tines 60 decreases the pressure exerted upon the upper surface of retina 30 by the rake 10. For example, in one embodiment, when the tines 60 are fully extended and contacting the membrane 20, the handle 40 can be moved downward toward the retina 30 up to a millimeter without any significant or noticeable force on the retina 30. Such flexibility reduces the risk of injury to the eye during use of the rake 10. The flexibility of the tines 60 can be decreased, that is, the tines 60 can be made stiffer, by simply retracting the tines 60 into the handle 40 until a desired stiffness is reached.

Figure 10:
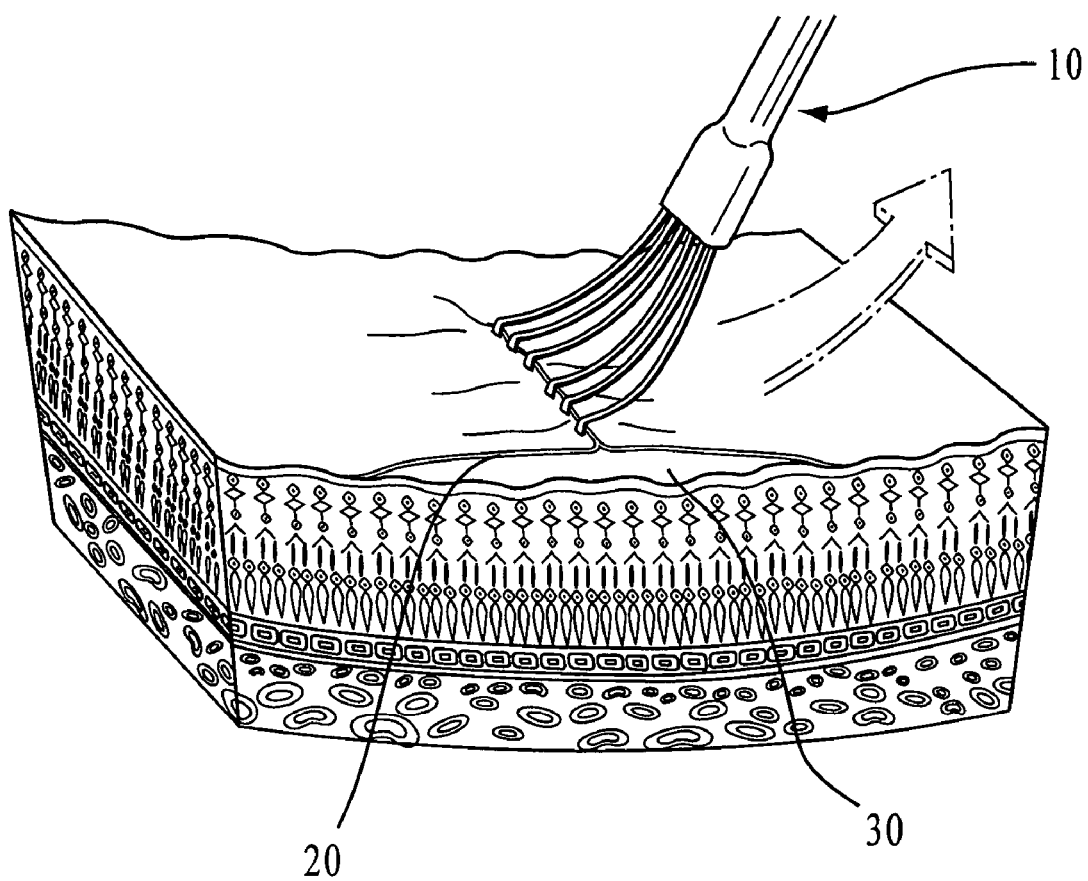
FIG. 10 illustrates the rake engaging the membrane in an intermediate portion of the membrane remote from the peripheral edges of the membrane.

FIG. 10 illustrates the ability of the rake 10 to engage the membrane 20 at a location along the inner surface of the membrane 20, with the location not being required to include an outer edge of the membrane 20 to be removed. The rake 10 is dragged along the upper surface of membrane 20 until the tissue engaging features 70 and 70' engage the surface of the membrane 20. Once the tissue engaging features 70 and 70' engage the membrane surface, the rake 10 is simply pulled upward and tangentially away from the upper surface of the retina 30 to remove the membrane 20 therefrom. Once the rake 10 engages the membrane 20, no additional downward force is exerted upon the retina 30, which reduces the risk of eye injury.

Example embodiments of the present invention have now been described in accordance with the above advantages. It will be appreciated that these examples are merely illustrative of the invention. Many variations and modifications will be apparent to those skilled in the art without departing from the scope and spirit of the invention.

What is claimed is:

1. An internal limiting membrane rake for microsurgical applications, the rake being sizably configured for insertion into an eye, and engagement with and selective removal of intraocular membrane, the rake comprising:
    a rake body having an opening;
    a slide member slidable within the rake body opening; and
    a plurality of tines extendable via the slide member through the opening in the rake body, the plurality of tines being attached to the slide member so as to spread apart relative to one another during extension via the slide member and to draw together during retraction into the rake body opening, wherein each tine includes:
        at least one tissue engaging element provided at one end of the tine, each tissue engaging element extending in an extension direction, the at least one tissue engaging element including a tissue engagement feature configured for removal of membrane from the outer surface of an eye retina, wherein the tissue engagement feature comprises at least one sharp barb;
    wherein the extension directions of the plurality of tissue engaging elements are configured for contemporaneous engagement of the plurality of tissue engaging elements with the outer surface of the retina from a single direction; and wherein the plurality of tines are configured to graspably retain the removed membrane from the outer surface of the eye retina.

2. The rake according to claim 1, wherein the rake body has a shape in cross-section that is selected from a group consisting of oval, rectangular, trapezoidal, and hemispherical.

3. The rake according to claim 1, wherein each tine is flexible and has a degree of flexing that increases the further the slide member extends from the rake body.

4. The rake according to claim 1, wherein each of the plurality of tines extends away from a neighboring tine in a direction substantially radial relative to a longitudinal axis of the rake body and within a single plane when the plurality of tines are in a fully extended state relative to the rake body and unengaged with the outer surface of the retina.

5. The rake according to claim 1, wherein each of the at least one tissue engaging element has a curved shape.

6. An internal limiting membrane rake for microsurgical applications, the rake being sizably configured for insertion into an eye, and engagement with and selective removal of intraocular membrane, the rake comprising:
    a rake body having an opening;
    a slide member slidable within the rake body opening; and
    a plurality of tines extendable via the slide member through the opening in the rake body, the plurality of tines being attached to the slide member so as to spread apart relative to one another during extension via the slide member and to draw together during retraction into the rake body opening, wherein each tine includes:
        at least one tissue engaging element provided at one end of the tine, each tissue engaging element extending in an extension direction, the at least one tissue engaging element including a tissue engagement feature configured for removal of membrane from the outer surface of an eye retina, wherein the tissue engagement feature comprises a serrated end;

wherein the extension directions of the plurality of tissue engaging elements are configured for contemporaneous engagement of the plurality of tissue engaging elements with the outer surface of the retina from a single direction; and wherein the plurality of tines are configured to graspably retain the removed membrane from the outer surface of the eye retina.

7. A membrane rake for use in microsurgery for removing a portion of an eye retina, the membrane rake being sizably configured for insertion into the eye, and engagement with and removal of intraocular membrane, the membrane rake comprising:

a body portion; and a tine extension mechanism moveable within the body portion, the tine extension mechanism having a plurality of tines attached thereto, each of the plurality of tines having a direction of extension;

wherein the plurality of tines are extendable from the body portion, wherein the plurality of tines are configured to spread radially such that the plurality of tines fall within a single plane in the direction of extension when fully extended from the body portion, the spread of the plurality of tines being variable via movement of the tine extension mechanism relative to the body portion, and wherein each of the plurality of tines has a sharp barb extending therefrom in a barb extension direction, the sharp barb being oriented to engage the membrane of the surface of the retina such that the extension direction is normal to the surface of the retina; and wherein the plurality of tines are configured to graspably retain the removed membrane from the outer surface of the retina.

8. The membrane rake of claim 7, wherein the body includes an opening, and wherein the tine extension mechanism comprises a slide receivable in the opening.

9. The membrane rake of claim 7, wherein the plurality of tines are retractable within the body.

10. The membrane rake of claim 7, wherein the barb extension direction of the sharp barb for each tine extends approximately perpendicularly to the direction of extension of the tine from which the barb extends.

11. The membrane rake of claim 7, wherein the tine extension mechanism is lockable at a fixed position relative to the body.

12. The membrane rake of claim 11, wherein the tine extension mechanism is lockable via friction.

13. The membrane rake of claim 7, wherein extension of the plurality of tines is controlled by one selected from a group consisting of mechanical control, hydraulic control, and electromechanical control.

14. The membrane rake of claim 7, wherein the plurality of tines are able to flex, the magnitude of flex varying with the degree of extension relative to the body.

15. A microsurgical membrane rake, the rake being sizably configured for insertion into an eye, and engagement with and selective removal of intraocular membrane, the rake comprising:

a rake body having an opening;

a plurality of tines slidably retractable within the opening of the rake body, each of the plurality of tines including:

a tine extension having a direction of extension;

a tissue engaging feature oriented approximately normally to the direction of extension of the tine extension, wherein the tissue engaging feature includes one or more sharp barbs or serrated ends; and a slide, the plurality of tines being attached to the slide and configured such that each of the plurality of tines extends away from each of the other of the plurality of tines so as to spreadably distribute the plurality of tines upon the plurality of tines being extended from the rake body, the distributed tines spreadably distributing so as to allow engagement of all of the tissue engaging features of the plurality of tines with an eye surface in a direction normal to the eye surface; and wherein the plurality of tines are configured to graspably retain the removed membrane from the outer surface of the eye.

16. The membrane rake of claim 15, wherein the rake body comprises a handle.

17. A microsurgical membrane rake for use with membrane of an eye retina, the rake being sizably configured for insertion into the eye, and engagement with and selective removal a portion of the membrane, the membrane rake comprising:

a handle; and a sliding extension receivable in the handle, the sliding extension having a plurality of membrane engaging extensions connected thereto;

wherein the plurality of membrane engaging extensions each comprise at least one sharp barb or serrated end and are extendable from the handle;

wherein the membrane engaging extensions are attached to the sliding extension so as to orient and spread relative to one another, the extension and spreading of the plurality of membrane engaging extensions being variably controllable via movement of the sliding extension relative to the handle; and wherein, when engaged with a membrane, the membrane engaging extensions are manipulable to create tangential and lifting forces to remove a portion of the membrane of the eye retina.

18. An internal limiting membrane rake for microsurgically removing a membrane from a surface of an eye retina, the rake comprising:

a handle having an opening;

a telescoping slide member receivable in the opening of the handle; and a plurality of tines extending radially from one end of the slide member, wherein each tine includes at least one tissue engaging element provided at one end of the tine, and wherein each of the at least one tissue engaging element includes:

a flexible body portion having a longitudinal direction; and an engaging portion that includes at least one sharp barb or serrated end the engaging portion extending substantially perpendicularly to the longitudinal axis in a direction of extension parallel to that of at least one other engaging portion; and wherein the plurality of tines are configured to graspably retain the removed membrane from the outer surface of the eye retina.

* * * * *